(12) United States Patent
Castle

(10) Patent No.: US 11,538,584 B2
(45) Date of Patent: Dec. 27, 2022

(54) AUTOBOT SECURITY PORTAL AND MOBILE SANITIZER

(71) Applicant: Michael C Castle, Capitola, CA (US)

(72) Inventor: Michael C Castle, Capitola, CA (US)

( * ) Notice: Subject to any disclaimer, the term of this patent is extended or adjusted under 35 U.S.C. 154(b) by 401 days.

(21) Appl. No.: 15/931,189

(22) Filed: May 13, 2020

(65) Prior Publication Data

US 2021/0358621 A1    Nov. 18, 2021

(51) Int. Cl.
*A61B 5/01* (2006.01)
*A61B 5/00* (2006.01)
*G16H 50/20* (2018.01)
*G16H 50/80* (2018.01)

(52) U.S. Cl.
CPC .......... *G16H 50/20* (2018.01); *A61B 5/0059* (2013.01); *A61B 5/01* (2013.01); *G16H 50/80* (2018.01)

(58) Field of Classification Search
CPC ...... G16H 50/20; G16H 50/80; A61B 5/0059; A61B 5/01
See application file for complete search history.

(56) References Cited

U.S. PATENT DOCUMENTS

| | | | | |
|---|---|---|---|---|
| 6,338,715 B1 * | 1/2002 | Hayes | ................ | A61B 5/4011 600/303 |
| 10,570,577 B2 * | 2/2020 | Kramer | .................. | E01F 13/08 |
| 10,902,955 B1 * | 1/2021 | Federoff | ........... | A61B 5/02405 |
| 11,170,894 B1 * | 11/2021 | Kocher | ................ | A61B 5/1176 |
| 2005/0074086 A1 * | 4/2005 | Pendergraft | ............. | B64F 1/30 378/6 |
| 2005/0210578 A1 * | 9/2005 | O'Brien | ................. | A47K 3/286 4/615 |
| 2011/0131054 A1 * | 6/2011 | Theobald | .............. | G16H 40/20 235/375 |
| 2012/0075053 A1 * | 3/2012 | Rayner | .................. | E05F 15/70 340/3.1 |
| 2012/0306651 A1 * | 12/2012 | Hall | ................... | G08B 13/2454 340/572.1 |
| 2016/0317686 A1 * | 11/2016 | Dayton | ..................... | A61L 2/10 |
| 2017/0332055 A1 * | 11/2017 | Henderson | ........ | G07C 9/00174 |
| 2019/0213817 A1 * | 7/2019 | Wechsler | ........... | G07C 9/00563 |
| 2020/0327759 A1 * | 10/2020 | Neiman | ................... | G07C 9/28 |
| 2021/0335073 A1 * | 10/2021 | Luker | .................... | G07C 9/257 |

* cited by examiner

*Primary Examiner* — John R Downey
(74) *Attorney, Agent, or Firm* — Donald R. Boys; Central Coast Patent Agency, LLC

(57) ABSTRACT

A security portal has a body having sidewalls and a top, a floor, and an entrance passageway, a remotely operable entrance barrier at the entrance passageway, a remotely operable exit barrier at the exit passageway, input apparatus in the security portal, an optical temperature sensor positioned and remotely operable to sense the subject's skin temperature, and a computerized base station remote from the security portal. The operative opens the entrance barrier to admit the subject, uses the input apparatus to solicit information, performs an evaluation process involving identity and skin temperature, and, depending on result of the evaluation process, the operative opens the entrance barrier and asks the subject to leave through the entrance passageway, or opens the exit barrier and asks the subject to leave through the exit passageway into the secured area.

16 Claims, 2 Drawing Sheets

AUTOBOT SECURITY PORTAL AND MOBILE SANITIZER

BACKGROUND OF THE INVENTION

1. Field of the Invention

The present invention is in the technical area of apparatus for security passage and pertains more particularly to a portal for sensing probability of infection and admitting or denying admission based on results.

2. Description of Related Art

At the time of filing the present patent application there is a world-wide pandemic related to the disease termed covid-19, for corona virus disease 2019. As is well-known, most business entities have been forced to close, from large corporate entities to small businesses of all sorts. As plans are made to reopen and to ty to return to a more normal social association and economy, many are concerned about being able to track whether or not individual persons may be infected.

The inventor in this case has surmised that an important issue for any enterprise in admitting customers and employees to a place of business is determining in some way whether the individual subjects have the disease, have been tested for the disease or may have symptoms related to the disease. A business owner or manager may require, for example, existing test results, administering new tests, or checking temperature, and other symptoms of the disease. These procedures may well be just too cumbersome for admission to an enterprise.

What is clearly needed is a portal that may be used to admit one subject at a time and may be operable to determine whether a subject admitted to the portal has or may have the disease, before passing the subject onto the premises.

BRIEF SUMMARY OF THE INVENTION

In an embodiment of the invention a security portal for gating subjects into a secured area is provided, comprising a body having sidewalls and a top, a floor, an entrance passageway having a width of at least three feet and height of at least six feet, and an exit passageway having a width of at least three feet and height of at least six feet, a remotely operable entrance barrier at the entrance passageway operable to open to admit a subject and to close after admitting the subject, a remotely operable exit barrier at the exit passageway operable to open to release the subject and to close after releasing the subject, input apparatus in the security portal adapted to receive input from the subject in the security portal regarding identity of the subject, an optical temperature sensor positioned and remotely operable to sense the subject's skin temperature with the subject in the security portal, and a computerized base station remote from the security portal, adapted for an operative to manipulate the remotely operable elements of the security portal, and to communicate with the subject in the security portal. The operative utilizes the control apparatus to open the entrance barrier to admit the subject to the security portal, utilizes the input apparatus to solicit information identifying the subject having entered the security portal, performs an evaluation process involving activating the optical temperature sensor indicating the subject's skin temperature, and, depending on result of the evaluation process, the operative opens the entrance barrier and asks the subject to leave through the entrance passageway, or opens the exit barrier and asks the subject to leave through the exit passageway into the secured area.

In one embodiment the security portal further comprises a scent system operable to emit a scented vapor within the security portal, wherein the operative, as a part of the evaluation process, causes a scent to be emitted into the security portal, and asks the subject for recognition of the scent. Also, in one embodiment the security portal further comprises one or more germicidal lamps positioned and operable to illuminate the subject when in the security portal, wherein the lamps illuminate during the time the subject is in the security portal. In one embodiment the portal further comprises computerized circuitry adapted to communicate with the base station and a microphone and a speaker, and wherein the base station executes software (SW) displaying interactive interfaces enabling the operative to communicate with the subject in the security portal via the microphone and speaker, and to manipulate the remotely operable elements of the security portal. And in one embodiment the portal further comprises imaging apparatus in the security portal enabling the operative to image the subject in the security portal, and a touchscreen adapted for biometric input from the subject.

In one embodiment of the invention the portal further comprises a deployable and retractable drive system comprising drive wheels enabling the security portal, with the drive wheels deployed to be translated along a surface according to programmed pathways. In one embodiment the portal further comprises a tank of pressurized germicidal solution and a wand and a nozzle, enabling spraying of germicidal vapor during translation of the security portal along the surface. In one embodiment the portal further comprises germicidal lights on deployable wands that, deployed, illuminate articles and surfaces along the programmed pathways. In one embodiment one or more of the wands deployed extend horizontally proximate the surface along the programmed pathways, such that the surface is illuminated. And in one embodiment the portal further comprises imaging devices and sensors implemented on outside surfaces of the body of the security portal, enabling the operative and the software at the base station to guide the security portal in translation.

In another aspect of the invention a method for gating subjects into a secured area is provided, comprising placing a security portal with a body having sidewalls and a top, a floor, an entrance passageway having a width of at least three feet and height of at least six feet, and an exit passageway having a width of at least three feet and height of at least six feet, at an entranceway into a secured area, opening a remotely operable entrance barrier at the entrance passageway by an operative at a computerized base station remote from the security portal, adapted for an operative to manipulate the remotely operable elements of the security portal, and to communicate with the subject in the security portal, admitting a subject into the security portal, then closing the entrance barrier, soliciting by the operative identity of the subject through input apparatus in the security portal, activating by the operative an optical temperature sensor positioned and remotely operable to sense the subject's skin temperature with the subject in the security portal, sensing the skin temperature of the subject, determining if the subject should be passed into the secured area, depending on the identity of the subject and the skin temperature of the subject, and, if the determination is that the subject should be passed, opening a remotely operable exit barrier, enabling the subject to pass into the secured area, or, if the determination is that the subject should not be passed, opening again the entrance barrier and asking the subject to leave the security portal through the entrance barrier.

In one embodiment the method further comprises emitting a scent a scented vapor within the security portal and asking the subject to identify the scent as a part of determining whether the subject should be passed into the secured area. Also, in one embodiment the method further comprises activating one or more germicidal lamps positioned and operable to illuminate the subject when in the security portal. In one embodiment the method further comprises communicating by the operative with the subject in the security portal using computerized circuitry executing software (SW) displaying interactive interfaces enabling the operative to communicate with the subject in the security portal via a microphone and a speaker. And in one embodiment the method further comprises imaging the subject in the security portal, using imaging apparatus in the security portal, and a soliciting input from the subject by a touch-screen adapted for biometric input from the subject.

In one embodiment the method further comprises deploying a deployable and retractable drive system comprising drive wheels under the security portal and translating the security portal along a surface according to programmed pathways. In one embodiment the method further comprises spraying germicidal vapor from a tank of pressurized germicidal solution having a wand and a nozzle, during translation of the security portal along the surface. In one embodiment the method further comprises deploying germicidal lights on deployable wands that illuminate articles and surfaces along the programmed pathways. In one embodiment the method further comprises deploying one or more of the wands to extend horizontally proximate the surface along the programmed pathways, such that the surface is illuminated. And in one embodiment the method further comprises guiding the security portal in translation using imaging devices and sensors implemented on outside surfaces of the body the security portal.

DETAILED DESCRIPTION OF THE INVENTION

In embodiments of the invention a portal apparatus is provided that has turnstile mechanisms to admit subjects into the portal, and to pass the same subjects through the portal, and has functionality to determine with a relatively high probability of fact that the subject may be infected with Covid-19.

Figure 1:
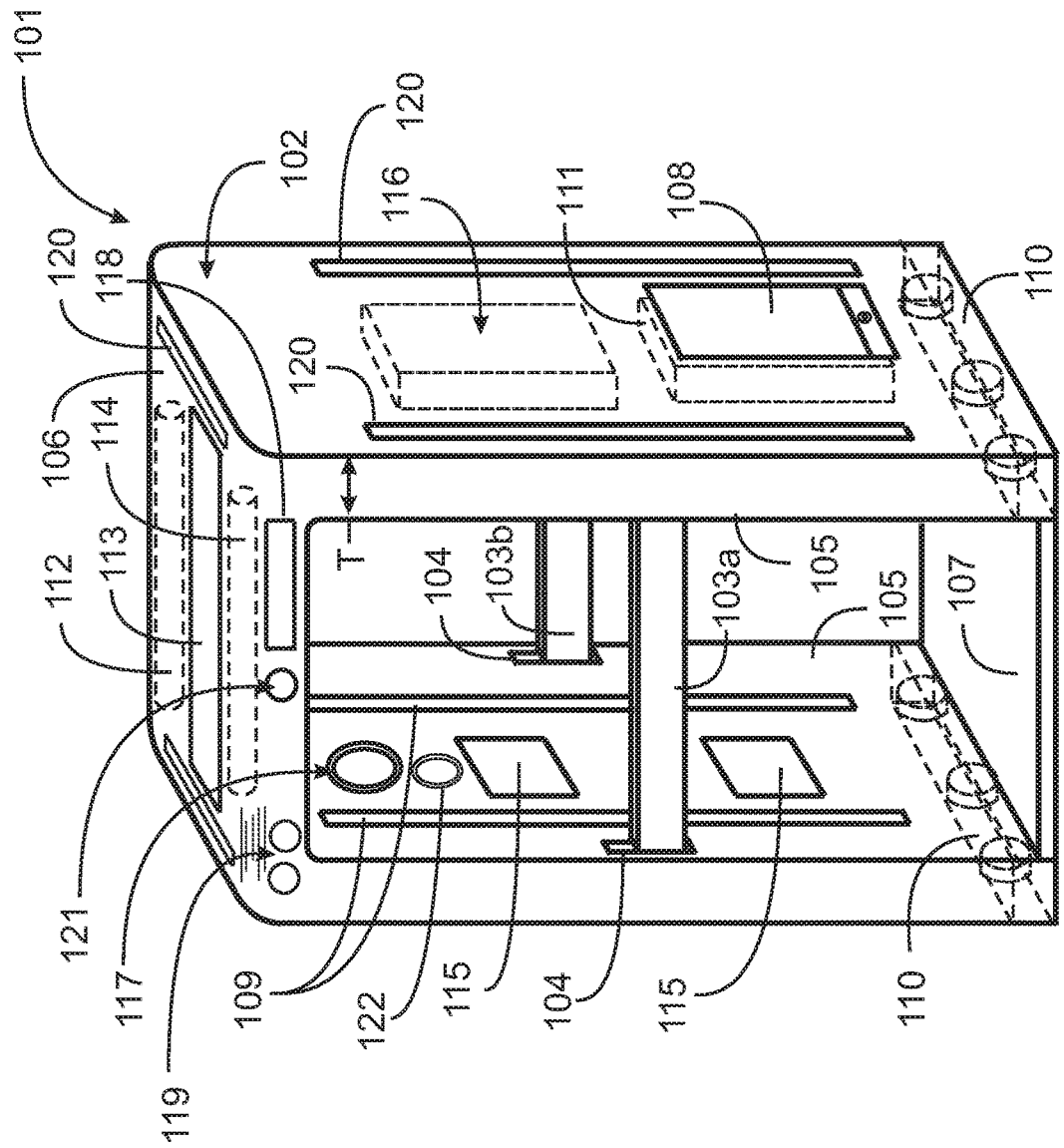
FIG. 1 is a perspective view of a portal apparatus in an embodiment of the present invention.

FIG. 1 is a perspective view of a portal apparatus 101 in an embodiment of the invention. The portal apparatus in this example has a body 102 that provides entrance and exit passages, turnstiles, and houses a considerable variety of functional equipment, including electronics, as is described in enabling detail below. The body in this example is implemented by aluminum panels over a fiberglass or carbon fiber frame, to minimize weight. In alternative embodiments the frame may be aluminum or steel and the panels of plastic or another metal. In this example has walls 105 having a wall thickness T, which may be several inches in thickness, providing sufficient internal space to house a number of mechanical mechanisms as well as power supplies and electrical and electronic circuitry. This wall thickness applies to a top 106 of the portal as well as to the two sides. T in one embodiment may be about six inches but may be larger or smaller in other embodiments.

Body 102 is open in the front and the back providing passage through the portal apparatus over a sturdy floor 107. An important function of the portal apparatus is to provide a gating operation at a door or other entrance and exit point in a building, such that subjects may be admitted, processed and either turned away or passed through, depending on results of the processing.

To facilitate processing subjects there are in this example an entrance barrier 103a and an exit barrier 103b. These barriers in this example are pivoted on one end, and, upon rotating to a horizontal position enter slots 104 on an inside wall of the portal, where locking mechanisms may be activated to lock the barriers so they may not be manually raised. A person of ordinary skill will understand that there are alternative ways these barriers may be implemented to provide the necessary gating function.

In one embodiment there are germicidal ultraviolet lamps implemented in the portal apparatus. These lamps in this example are recessed in channels 109, on both internal walls and on the inside ceiling of the portal. Power for the germicidal lamps is provided from within the walls. In this embodiment there may be channels 120 implemented in the outer walls of the portal apparatus, with germicidal lamps recessed in the channels, and individually controllable. The lamps in channels 120 are mounted on wands pivoted at the lower end such that the wands may be deployed with the apparatus in a mobile application, to extend over the floor or ground surface.

When not being utilized as a portal the apparatus may be a self-driving sanitation unit in a facility with preprogrammed autopilot and GPS capability, and may spray and otherwise dispense antibiotic and anti-viral materials in the associated facility. Pursuant to this purpose, the portal apparatus in this example has opposite sets of retractable and extendable drive wheels 110, shown in hidden lines, as the wheels are retracted up into the opposite walls of the apparatus by remotely operable mechanisms. The drive wheels are driven by DC electric motors in one embodiment, connected to power lines from a battery pack described below. The wheels are mounted on mechanisms such that the wheels may be manipulated to drive the portal in different directions.

The operating elements of the portal are powered in this example by a removable Lithium Ion battery pack 111 implemented behind a panel 108. A charging cord for the rechargeable battery is also stored in the compartment behind panel 108.

In one embodiment of the invention, scents are dispensed as a part of an evaluation of a subject in the portal, and the subject is asked if a scent is detected, and if so, if the subject can identify the scent. It is known that one of the symptoms of Covid-19 is an impairment of the olfactory sense. In this example there are two tanks, 112 and 114. Tank 112 is devoted to scents. There are two separate compartments, each storing a separate scented material. The tank compartments are connected to conduits with valves and dispenser nozzles, which are remotely operable to spray a small amount of each scent liquid into the air in the portal on command of an operator. Tank 114 is devoted to a germicidal solution for spraying in either portal or mobile mode.

Also, in this embodiment a solar panel 113 is implemented on a top surface of the portal body. This panel is representative and exemplary, as there may be more solar panels implemented on other surfaces of the body of the portal. These panels are connected to circuitry for recharging battery pack 111 in this example. Portal 101 is made to be used either indoors or outdoors, and in outdoor applications the solar panels are useful. In some circumstances, for example, portals according o embodiments of this invention may be used at outdoor gates in fences and the like, for admission to certain areas and regions.

In the embodiment illustrated in FIG. 1 there are implemented two touchscreen displays 115 with six-inch screens at two adjustable heights on one internal wall of the portal. Displays 115 may be operated as biometric inputs for such as fingerprint scanning and may also be used to display messages for subjects, and to ask questions pertinent to Covid-19 possibility of infection.

Also mounted on an inside wall there may be another imaging device 122 devoted to face-recognition and thermal imaging, for recognizing subjects and checking external body temperature.

Figure 2:
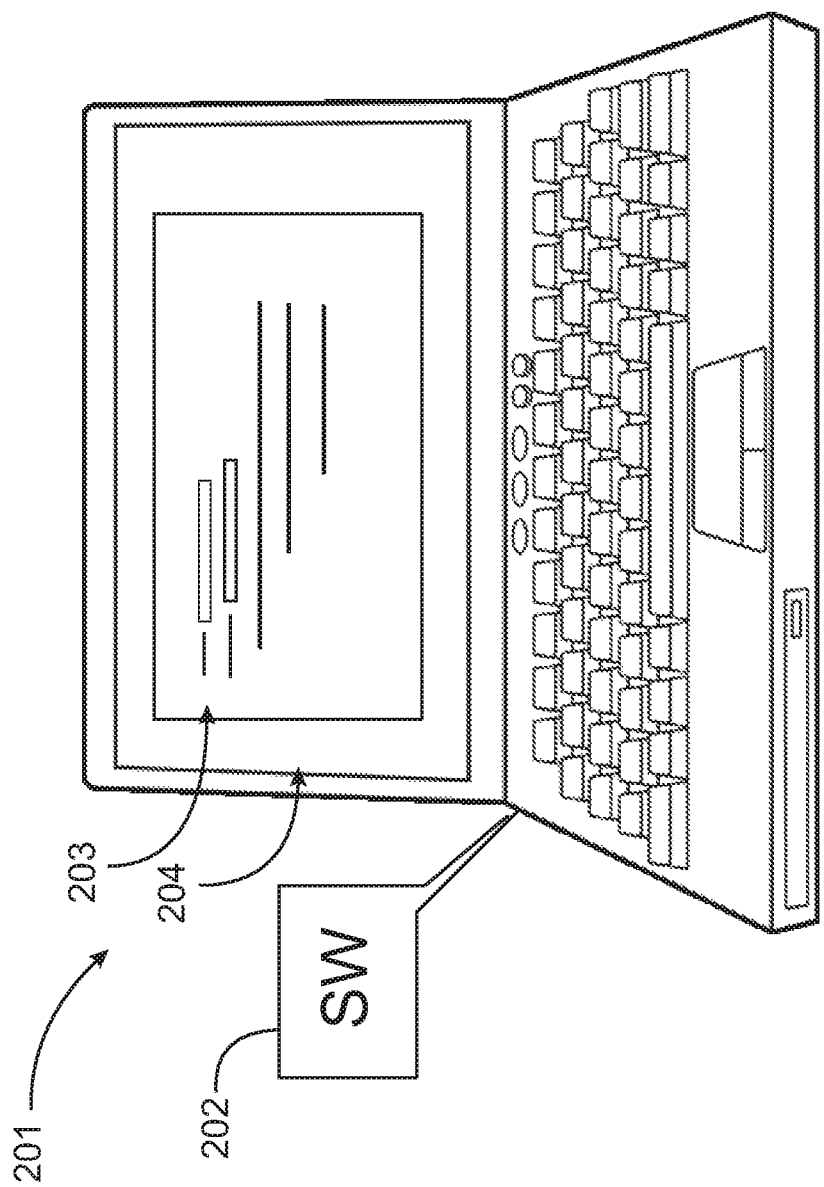
FIG. 2 illustrates a remote-control base station in an embodiment of the invention.

Computerized circuitry 116 in a compartment in a wall of the portal comprising at least a CPU, digital memory elements, wireless communication elements for wireless communication with a local base station and hand-held portable devices. A local base station may be a laptop computer 201 with an application providing command input for the portal, as shown in FIG. 2. Software (SW) 202 executing on a CPU of computer 201 provides interactive interfaces such as interface 203 on display 204 of computer 201, through which operating personnel may operate mechanisms of the portal apparatus, such as, for example, the movable barriers 103a and 103b. Interactive interface 203 comprises input fields through which an operative may input information or data, such as messages to be displayed. Links may be provided for operating commands, such as to open and close barriers, or to emit a scent. A microphone of the computer and speakers may provide two-way voice communication with a subject in the portal.

SW 202 may also provide face-recognition for images transmitted from cameras 121.

A skilled person will understand that control capability is not limited to a laptop computer as described as an example but may be implemented at a remote location with any one of a variety of computerized equipment, for control of portal apparatus 101. Further, communication and control may be linked through base stations to a plurality of portals like portal apparatus 101. In some embodiments there may a control interface implemented directly on the portal apparatus with command inputs to control functions of the portal apparatus, in addition to, or instead of, the more remote-control system comprising the computer 201.

A communication port 117 on an inside wall of portal apparatus 101 comprises a sensitive microphone, a speaker, and in some embodiments an imaging apparatus and circuitry that may include still photography, video, and wireless capability to stream real-tine video to the computer in the base station.

In this embodiment there are two digital, programmable WIFI LED message boards 118, one clearly visible at the entry point and another at the exit point. These message boards may be used to display messages intended by operating personnel for subjects to be gated through the portal.

In one embodiment there may be lights 119, one red and one green, on a front and a rear surface of the body of the portal, that may be utilized to signal a subject to enter or not enter the portal from either side. There may also be thermal and face-recognition cameras 121 on front and rear surfaces on the body of the portal.

In one embodiment there may be deployable germicidal lamp wands in recesses 120 on the top, and in some embodiments elsewhere on the body of the portal, that may be hinged at one end such that they be deployed.

In one embodiment the portal may be mobile. In this embodiment drive wheels 110 may be activated to raise the portal of the ground or paved surface, and the portal may be translated along the surface, such as within hallways and office facilities, and the portal may be thus utilized as a mobile sanitization robot. The portal in this mode may be programmed to follow installed cable pathways, or may be piloted by GPS and programmed patterns, or may be piloted by an operative utilizing interfaces on a control computer, such as computer 201. In this sanitization mode deployable germicidal wands may be deployed and powered, and in some embodiments sanitization fluids and vapors may be dispensed from outlets on the portal apparatus.

In one embodiment of the security portal of the invention functionality may be provided to conduct one or more sorts of virus tests, for presence of the Covid-19 virus for example, or for other viruses, such as any one of the various influenza strains.

In one embodiment any apparatus needed to self-administer a test might be provided at the entrance to the security portal, and a subject may take the kit into the portal. The subject might then self-administer the test and report the result to the base station via any available communication channel. In another variation, there may be a test technician posted at the entrance to the portal who might perform the test on the subject about to enter the portal.

In yet another variation tests may be incorporated into the apparatus of the portal, and a subject may be guided through administration of the test by an operative at the base station, or by recorded instructions.

The inventor is aware that tests of this sort may take at the least several minutes to perform and verify, and that this timing factor may be incompatible with the purpose of quickly and efficiently gating subjects through the portal. In these circumstances the test may be recorded, and results matched with records for subjects when results become available.

In some circumstances, if an antibody test indicated that a subject might be immune, an immunity card might be issued to the subject by apparatus integrated with the security portal.

A person of ordinary skill will understand that the embodiments described above are exemplary, and not limiting to the scope of the invention and further that elements of the apparatus and functionality described might be claimed in any combination from descriptions of embodiments above. Scope of the invention is limited only by claims.

The invention claimed is:
1. A security portal, comprising:
a body having sidewalls and a top, a floor, an entrance passageway having a width of at least three feet and height of at least six feet, and an exit passageway having a width of at least three feet and height of at least six feet;
a remotely operable entrance barrier at the entrance passageway operable to open to admit a subject and to close after admitting the subject;

a remotely operable exit barrier at the exit passageway operable to open to release the subject and to close after releasing the subject;

input apparatus in the security portal adapted to receive input from the subject in the security portal regarding identity of the subject;

an optical temperature sensor positioned and remotely operable to sense the subject's skin temperature with the subject in the security portal;

a deployable and retractable drive system comprising drive wheels enabling the security portal, with the drive wheels deployed to be translated along a surface according to programmed pathways:

a tank of pressurized germicidal solution and a wand and a nozzle, enabling spraying of germicidal vapor during translation of the security portal along the surface; and a computerized base station remote from the security portal, adapted for an operative to manipulate the remotely operable elements of the security portal, and to communicate with the subject in the security portal.

2. The security portal of claim 1 further comprising a scent system operable to emit a scented vapor within the security portal.

3. The security portal of claim 1 further comprising one or more germicidal lamps positioned and operable to illuminate the subject when in the security portal, wherein the lamps illuminate during the time the subject is in the security portal.

4. The security portal of claim 1 further comprising computerized circuitry adapted to communicate with the base station and a microphone and a speaker, and wherein the base station executes software (SW) displaying interactive interfaces enabling the operative to communicate with the subject in the security portal via the microphone and speaker, and to manipulate the remotely operable elements of the security portal.

5. The security portal of claim 1 further comprising imaging apparatus in the security portal enabling the operative to image the subject in the security portal, and a touchscreen adapted for biometric input from the subject.

6. The security portal of claim 1 further comprising germicidal lights on deployable wands that, deployed, illuminate articles and surfaces along the programmed pathways.

7. The security portal of claim 6 wherein one or more of the wands deployed extend horizontally proximate the surface along the programmed pathways, such that the surface is illuminated.

8. The security portal of claim 1 further comprising imaging devices and sensors implemented on outside surfaces of the body of the security portal, enabling the operative and the software at the base station to guide the security portal in translation.

9. A method, comprising:

placing a security portal with a body having sidewalls and a top, a floor, an entrance passageway having a width of at least three feet and height of at least six feet, and an exit passageway having a width of at least three feet and height of at least six feet, at an entranceway into a secured area;

opening a remotely operable entrance barrier at the entrance passageway by an operative at a computerized base station remote from the security portal, adapted for an operative to manipulate the remotely operable elements of the security portal, and to communicate with the subject in the security portal, admitting a subject into the security portal, then closing the entrance barrier;

soliciting by the operative identity of the subject through input apparatus in the security portal;

activating by the operative an optical temperature sensor positioned and remotely operable to sense the subject's skin temperature with the subject in the security portal, sensing the skin temperature of the subject;

determining if the subject should be passed into the secured area, depending on the identity of the subject and the skin temperature of the subject;

if the determination is that the subject should be passed, opening a remotely operable exit barrier, enabling the subject to pass into the secured area, or, if the determination is that the subject should not be passed, opening again the entrance barrier and asking the subject to leave the security portal through the entrance barrier;

deploying a deployable and retractable drive system comprising drive wheels under the security portal and translating the security portal along a surface according to programmed pathways; and spraying germicidal vapor from a tank of pressurized germicidal solution having a wand and a nozzle, during translation of the security portal along the surface.

10. The method of claim 9 further comprising emitting a scented vapor within the security portal and asking the subject to identify the scent as a part of determining whether the subject should be passed into the secured area.

11. The method of claim 9 further comprising activating one or more germicidal lamps positioned and operable to illuminate the subject when in the security portal.

12. The method of claim 9 further comprising communicating by the operative with the subject in the security portal using computerized circuitry executing software (SW) displaying interactive interfaces enabling the operative to communicate with the subject in the security portal via a microphone and a speaker.

13. The method of claim 9 further comprising imaging the subject in the security portal, using imaging apparatus in the security portal, and a soliciting input from the subject by a touchscreen adapted for biometric input from the subject.

14. The method of claim 9 further comprising deploying germicidal lights on deployable wands that illuminate articles and surfaces along the programmed pathways.

15. The method of claim 14 further comprising deploying one or more of the wands to extend horizontally proximate the surface along the programmed pathways, such that the surface is illuminated.

16. The method of claim 9 further comprising guiding the security portal in translation using imaging devices and sensors implemented on outside surfaces of the body the security portal.

* * * * *